US011708322B2

(12) United States Patent
Kataria et al.

(10) Patent No.: US 11,708,322 B2
(45) Date of Patent: Jul. 25, 2023

(54) PROCESS FOR PREPARATION OF 2,6-DICHLOROBENZONITRILE

(71) Applicant: Arysta LifeScience Inc., Cary, NC (US)

(72) Inventors: Kamal Kataria, Maharashtra (IN); Vic Prasad, Leawood, KS (US); Christopher Lynn Larson, Cary, NC (US); Cameron Seath Gibb, Apex, NC (US); Kirit Desai, Gujarat (IN); Ashwani Gupta, Gujarat (IN); Girish Sisode, Gujarat (IN)

(73) Assignee: ARYSTA LIFESCIENCE INC., Cary, NC (US)

( * ) Notice: Subject to any disclaimer, the term of this patent is extended or adjusted under 35 U.S.C. 154(b) by 0 days.

(21) Appl. No.: 16/685,703

(22) Filed: Nov. 15, 2019

(65) Prior Publication Data
US 2020/0157043 A1    May 21, 2020

Related U.S. Application Data

(60) Provisional application No. 62/768,407, filed on Nov. 16, 2018.

(51) Int. Cl.
 *C07C 253/30* (2006.01)
(52) U.S. Cl.
 CPC .................................. *C07C 253/30* (2013.01)

(58) Field of Classification Search
 None
 See application file for complete search history.

(56) References Cited

U.S. PATENT DOCUMENTS

| | | | |
|---|---|---|---|
| 3,265,603 A | 8/1966 | Franciscus et al. |
| 3,351,651 A | 11/1967 | Rothman et al. |
| 4,225,534 A | 9/1980 | Yoshikawa |
| 4,285,883 A | 8/1981 | Yoshikawa |

FOREIGN PATENT DOCUMENTS

| | | |
|---|---|---|
| CN | 103382166 A | 11/2013 |
| GB | 861898 | 3/1961 |
| GB | 861899 | 3/1961 |

OTHER PUBLICATIONS

International Search Report; International Application No. PCT/US2019/061792; dated Jan. 21, 2020; 4 pages.
Written Opinion; International Application No. PCT/US2019/061792; International Filing Date Nov. 15, 2019; dated Jan. 21, 2020; 7 pages.

*Primary Examiner* — Po-Chih Chen
(74) *Attorney, Agent, or Firm* — Cantor Colburn LLP

(57) ABSTRACT

Disclosed herein a process preparation of 2,6-dichlorobenzonitrile. A process of making high yield, high purity 2,6-dichlorobenzonitrile including the selective de-nitrochlorination of 2-chloro-6-nitrobenzonitrile by treatment of the 2-chloro-6-nitrobenzonitrile with chlorine gas.

7 Claims, No Drawings

PROCESS FOR PREPARATION OF 2,6-DICHLOROBENZONITRILE

TECHNICAL FIELD

The field of art to which this invention generally pertains is methods of making chemicals useful in insecticidal and herbicidal compositions. More, particularly the present invention relates to a process for preparation of halogenated benzonitriles.

BACKGROUND OF INVENTION

While many chemicals are known to be very effective raw materials for herbicidal and insecticidal applications, many require a significant investment in special equipment and/or costly raw materials to produce them. Because of the significant cost this can add to commercialization of these products, there is a constant search for ways to generate such products in more efficient and effective ways.

2,6-dichlorobenzonitriles also known as Dichlobenil, is a widely used herbicide in agriculture.

Various processes are known for synthesis of 2,6-Dichlorobenzonitrile via ammoxidation reaction. Known industrial methods for producing such material involve, such as vapor phase catalytic ammoxidation processing from 2,6-Dichlorotoluene, require a significant investment in equipment and there are limited sources for the costly raw material 2,6-dichlorotoluene.

U.S. Pat. No. 4,225,534 A discloses production of 2-chlorobenzonitrile derivatives by reacting with lithium chloride or a mixture of lithium chloride and anhydrous aluminum chloride or with lithium aluminum chloride in aprotic solvent making it industrially unfavorable.

Therefore, it is an object of the present invention to provide an improved method, which overcomes the above-mentioned disadvantages.

Accordingly, the present invention involves improvement in process with specific reaction parameters and objected to provide high selectivity, yield and purity of the desired product.

SUMMARY OF INVENTION

In an aspect the present invention provides, a simple and industrially viable process for producing halogenated benzonitriles.

In another aspect the present invention provides 2,6-dichlorobenzonitrile comprising treating 2-chloro-6-nitrobenzonitrile with chlorine gas.

In another aspect the present invention provides selective de-nitrochlorination synthesis of the 2-chloro-6-nitrobenzonitrile using chlorine in the absence of solvent.

In another aspect the present process provided controlled formation of by-products such as $NO_x$; 2-chlorobenzonitrile; 1,2,3-trichlorobenzonitrile; tetrachlorobenzene; and 2,6 difluorobenzamide leading to high yield and high purity desired product 2,6-dichlorobenzonitrile.

In an aspect the process of present invention provides 2,6-dichlorobenzonitrile in a high yield of at least 80% and purity of at least 99%.

These, and additional embodiments, will be apparent from the following descriptions.

DETAILED DESCRIPTION OF THE PRESENT INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise defined, "halogenated benzonitriles" are meant benzonitriles, which bear one or more halogen moieties, such as fluorine, chlorine, bromine or iodine atoms. A particular example is 2,6-dichlorobenzonitrile.

Notwithstanding that the numerical ranges and parameters setting, forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

The present invention provides a process for preparation of halogenated benzonitriles.

Accordingly, the present invention provides an efficient and effective process for the manufacturing of 2,6-Dichlorobenzonitrile.

The process of present invention is economically viable, it is very suitable to large-scale industrial production.

In an embodiment the process for preparation of 2,6-Dichlorobenzonitrile comprises de-nitrochlorination of 2-chloro-6-nitrobenzonitrile with chlorine gas.

The present process is represented by the following reaction scheme.

SCHEME 1

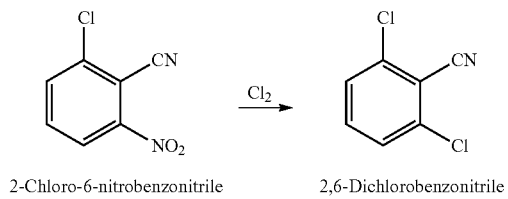

2-Chloro-6-nitrobenzonitrile     2,6-Dichlorobenzonitrile

In an embodiment the process for preparation of 2,6-Dichlorobenzonitrile comprises selective de-nitrochlorination of 2-chloro-6-nitroberizonitrile with chlorine gas without solvent.

In an embodiment the ratio of 2-chloro-6-nitrobenzonitrile and chlorine gas is in the range of 1:1 to 1:5.

In an embodiment the ratio of 2-chloro-6-nitrobenzonitrile and chlorine gas is in the range of 1:1 or 1:2 or 1:3 or 1:5.

In an embodiment, the process is carried out at temperature about 100 to 200° C.

In an embodiment, the process is carried out at temperature about 150 to 200° C.

In an embodiment, the process is carried out at 150° C. or at 155° C. or at 160° C. or at 165° C. or at 170° C. or at 175° C. or at 180° C. or at 185° C. or at 190° C. or at 195° C., In an embodiment the process is carried out for about 5 to 15 hours.

In an embodiment the process is carried out for about 8 to 10 hours.

In an embodiment the process is carried out at 185° C. to 195° C. for about 8 to 10 hours.

The process described above where the de-nitrochlorination takes place also forms $NO_x$ which is treated with acid for example concentrated sulfuric acid to form nitrosyl sulfuric acid. This nitrosyl sulfuric acid is can used for different purposes for example in diazotization and others known to a person skilled in the art.

In an embodiment the process provides enhanced control over formation of by-products, e.g., the over chlorinated by-products such as 1,2,3-trichlorobenzene, and tetrachlorobenzene (MB); reductive de-chlorination such as 2-chlorobenzonitrile; and hydrolysis products such as 2,6-difluorobenzamide as illustrated in Scheme 2.

SCHEME 2

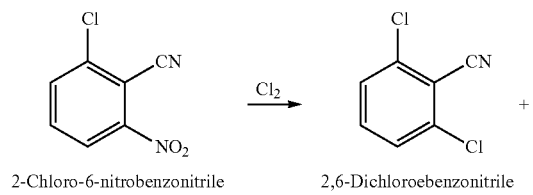

2-Chloro-6-nitrobenzonitrile     2,6-Dichloroebenzonitrile

-continued

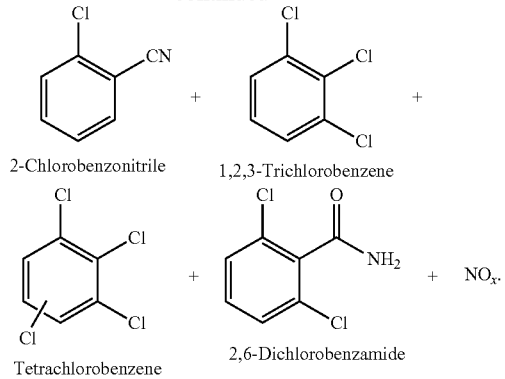

2-Chlorobenzonitrile     1,2,3-Trichlorobenzene

Tetrachlorobenzene     2,6-Dichlorobenzamide $+ NO_x$.

Accordingly, 2,6-Dichlorobenzonitrile obtained according to the present invention is substantially free from impurities.

Typically, 2,6-Dichlorobenzonitrile is substantially free of another compound when the other compound is present in an amount that is no more than 0.1%.

In an embodiment each byproduct or impurity formed in the process is limited to about less than 2%, preferably less than 1%, more preferably less than 0.1%.

In another embodiment, the 1,2,3-trichlorobenzene is the major impurity and the present process advantageously limited the formation of this impurity up to 2%, which can be further limited to less than 0.1% by purification methods.

In an embodiment 2,6-Dichlorobenzonitrile produced in high yield at least 80%, according to the present invention has high purity of at least 99% by selective de-nitrochlorination of 2-chloro-6-nitrobenzonitrile using chlorine gas under specific process parameters.

In an embodiment, the reactant itself act as solvent for reaction and the reaction proceeds without solvent.

The reaction takes place under approximately atmospheric pressure, which of course can also include slightly above and slightly below atmospheric conditions.

In the process of de-nitrochlorination of 2-chloro-6-nitrobenzonitrile controlling the introduction of the chlorine gas allows $NO_x$ (such as NO and $NO_2$, for example) to exit the system on a continuous basis as well.

2-Chloro-6-nitrobenzonitrile is prepared by conventional cyanide exchange of 2,3-Dichloronitrobenzene, itself a byproduct of the 3,4-Dichloronitrobenzene process with disposable or alternate use issues at produced volumes. As such, the process described herein represents a viable commercial use for this former waste product.

Therefore, the present invention provides very high selectivity and yield substantially reducing industrial production cost and meeting the needs of large-scale industrial production.

The objective described herein is to limit chlorine purge at a rate to selectively convert 2-chloro-6-nitro benzonitrile to 2,6-dichlorobenzonitrile and to limit the other side reactions which take place. An additional option is to improve selectivity by reactive distillation to separate out of the 2,6-dichlorobenzonitrile from the reaction phase as soon as it thrills.

Table 1 demonstrates a comparison of controlled and uncontrolled chlorine addition rate.

TABLE 1

| Conversion | Uncontrolled, % | Controlled, % |
| --- | --- | --- |
| 2,6-Dichlorobenzonitrile | 85 | 91-96 |
| TCB (trichlorobenzene) | 8-10 | 0.8-2.0 |
| MNCB (mononitrocholorbenzene) | 1-2 | <0.1 |
| Additional impurities | 3-4 | 0.9-2 |

White crystalline solid 2,6-Dichlorobenzonitrile with yields of at least 80% and purity levels greater than 99% (by weight) was obtained after suitable work-up to remove all of above mentioned reaction impurities at the above levels after reaction using, e.g., conventional solvent washing techniques. This makes the product attractive on many levels by this route.

The NOx liberated during reaction is scrubbed into concentrated sulfuric acid to give solid Nitrosyl sulfuric acid which is used as salable diazotization reagent.

SCHEME 3

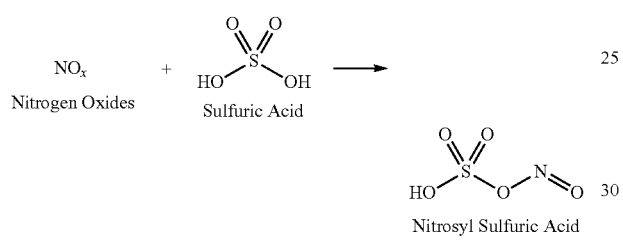

Thus, this represents an industrially advantageous and economically favorable process for manufacturing of 2,6-Dichlorobenzonitrile.

In another aspect the present invention provides a process for synthesis of 2,6-Dichlorobenzonitrile comprising the steps of
a) Preparation of 2-chloro-6-nitro benzonitrile
b) Optionally purification of 2-chloro-6-nitro benzonitrile
c) Preparation of 2,6-Dichlorobenzonitrile
d) Optionally purification of 2,6-Dichlorobenzonitrile In another aspect the present invention provides preparation of 2-chloro-6-nitro benzonitrile comprises reaction of 1,2-dichloro-3-nitro benzene with metal cyanide and/or metal chloride in presence of aprotic are to obtain 2-chloro-6-nitro benzonitrile.

In an embodiment the cyanation reaction is carried out by reacting 1,2-dichloro-3-nitro benzene with sodium cyanide and copper cyanide or sodium cyanide and copper chloride or a mixture of sodium cyanide, copper chloride and copper cyanide.

In an embodiment, the aprotic amides are selected from N,N-dimethylformamide, dimethylsulfoxide, N,N-dimethylacetamide, hexamethylphosphoramide and N-methylpyrrolidone and the like.

In an embodiment, the aprotic amides is N,N-dimethylformamide.

In an embodiment the process for preparation of 2-chloro-6-nitro benzonitrile comprising heating a mixture of 1,2-dichloro-3-nitro benzene, metal cyanide and aprotic amides as catalyst to obtain 2-chloro-6-nitro benzonitrile.

In another embodiment the process for preparation of 2-chloro-6-nitro benzonitrile comprising heating a mixture of 1,2-dichloro-3-nitro benzene, sodium cyanide and copper cyanide and dimethylformamide at temperature 100-200° C. to obtain 2-chloro-6-nitro benzonitrile.

In another embodiment the process for preparation of 2-chloro-6-nitro benzonitrile comprising heating a mixture of 1,2-dichloro-3-nitro benzene, sodium cyanide and copper chloride and dimethylformamide at temperature 100-200° C. to obtain 2-chloro-6-nitro benzonitrile.

In another embodiment the process for preparation of 2-chloro-6-nitro benzonitrile is carried out for 5-10 hours.

In another aspect the present invention provides preparation of 2-chloro-6-nitro benzonitrile comprises reaction of 1,2-dichloro-3-nitro benzene with metal cyanide and/or metal chloride in presence of aprotic amides to obtain 2-chloro-6-nitro benzonitrile.

In an embodiment, the process for preparation of 2,6-Dichlorobenzonitrile comprises
a) reaction of 1,2-dichloro-3-nitro benzene with metal cyanide and/or metal chloride or mixture thereof in presence of aprotic amides to obtain 2-chloro-6-nitro benzonitrile 2-chloro-6-nitro benzonitrile and
b) de-nitrochlorination of 2-chloro-6-nitrobenzonitrile with chlorine gas to obtain 2,6-dichlorobenzonitrile.

In another embodiment, the process for preparation of 2,6-Dichlorobenzonitrile comprises
) reaction of 1,2-dichloro-3-nitro benzene with metal cyanide and/or metal chloride or mixture thereof in presence of aprotic amides to obtain and
b) de-nitrochlorination of 2-chloro-6-nitrobenzonitrile with chlorine gas without solvent to obtain 2,6-Dichlorobenzonitrile.

The process condition and parameters are as described above.

The examples are merely illustrations and are not to be understood as limiting the scope and underlying principles of the invention in any way. Various modifications of the invention in addition to those shown and described herein will become apparent to those skilled in the art form after the following examples and foregoing description. Such modifications are also intended to fall within the scope of the appended claims.

EXAMPLES

Example 1

The process is following examples demonstrate the impact of temperature in the reaction.

TABLE 2

| Expt. | Temperature ° C. | Cl$_2$ Purging Time (hr) | Selectivity Towards 2,6-Dichlorobenzonitrile % | Yield % |
| --- | --- | --- | --- | --- |
| 1 | 150-155 | 8 | 67 | — |
| 2 | 170-175 | 16 | 90 | 74 |
| 3 | 190-195 | 9 | 96.48 | 81 |

In the above examples, nitrosyl sulfuric acid is produced and isolated as a solid from the sulfuric acid scrubber at molar equivalents to the NOx liberated.

Example 2

In 1 lit 4-neck RBF with overhead stirrer, TP, vigorous column and having Con. H$_2$SO$_4$ scrubber in an oil bath, 2-Chloro-6-nitro benzonitrile was charged and the temperature was raised. Then chlorine gas was purged slowly into the flask for consistent rate.

The resultant reaction mass was analyzed for 2,6-CNBN conversion to ≥99%; 2,6-Dichlorobenzonitrile observed as 73-80%; TCB as 9.4-10%.

After completion of reaction, the reaction mass was cooled to 100° C. and diluted with monochlorobenzene, neutralized by washing with 10% Aq. Sodium carbonate solution and decolorized with activated charcoal. This decolorized 2,6-Dichlorobenzonitrile solution was refluxed in methanol and crystallized at 10° C. filtered and dried in vacuum oven.

TABLE 3

| Example | (#) | 1 | 2 |
|---|---|---|---|
| CNBN | (mol) | 1.10 | 1.10 |
| Cl2 | (mol) | 2.19 | 2.19 |
| Reaction temp | (° C.) | 180 | 190 |
| Purging Time | (h) | 12 | 12 |
| Reaction mass | TCB | 9.4 | 10.09 |
| composition | DCBN | 80.04 | 73.49 |
|  | CNBN | 1.03 | 0.86 |
| Product Quality | TCB | 0.03 | 0.05 |
| (after work-up & | DCBN | 98.9 | 98.6 |
| crystallization) | CNBN | — | — |
| Yield of DCBN | (%) | 76.7 | 71.2 |

These examples demonstrate that DCBM can be prepared in 71-76% yield and >98% purity by denitrochlorination of CNBN at 180-190° C. utilizing controlled chlorine addition and in the absence of solvent.

Example 3-6

2-Chloro-6-nitro benzonitrile (obtained from the process described in example 7) was charged in RBF equipped with Cone, Sulfuric acid & caustic scrubber; Overhead stirrer & electrically heated Oil bath and the temperature was raised at 195° C. Then chlorine gas was purged for 10-16 hours in controlled order with varying rate. The resultant reaction mass was analyzed for 2,6-CNBN conversion to 99% & 2,6-Dichlorobenzonitrile showing 92-94%. The reaction mass was diluted with monochlorobenzene at 100° C.; neutralized by washing with 10% Aq. Sodium carbonate solution; decolorized with activated charcoal.

This decolorized 2,6-Dichlorobenzonitrile solution was refluxed in methanol and crystallized at 10° C., filtered and dried in vacuum oven.

TABLE 4

| Example | (#) | 3 | 4 | 5 | 6 |
|---|---|---|---|---|---|
| CNBN | (mol) | 10.9 | 9.9 | 9.9 | 9.9 |
| Cl2 | (mol) | 21.8 | 19.8 | 19.8 | 19.8 |
| Reaction temp | (° C.) | 190 | 190 | 190 | 190 |
| Purging Time | (h) | 11 | 14 | 16 | 11.5 |
| Reaction mass | TCB | 0.8 | 1 | 1.3 | 1.45 |
| composition | DCBN | 94.1 | 94.9 | 93.4 | 95.3 |
|  | CNBN | 1 | 0.6 | 0.2 | 0.87 |
| Product Quality | TCB | 0.005 | 0.001 | 0.08 | 0.03 |
| (after work-up & | DCBN | 99.9 | 99.94 | 99.75 | 99.8 |
| crystallization) | CNBN | — | — | — | — |
| Yield of DCBN | (%) | 75.2 | 79.8 | 79.8 | 79.8 |

This data shows that CNBN produced as described in example 7 increases the product content and yield because it reduces the incidence of TCB formation as observed for examples 1 and 2 above.

Example 7

Process for preparation of 2-Chloro-6-nitro benzonitrile

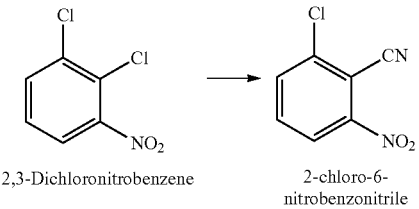 [SMILES: O=[N+]([O-])c1cccc(Cl)c1Cl ; N#Cc1c(Cl)cccc1[N+](=O)[O-]]

2,3-Dichloronitrobenzene        2-chloro-6-nitrobenzonitrile 2,3-Dichloronitrobenzene is charged with Sodium cyanide and copper cyanide or Sodium cyanide or Copper Chloride is charged in a 1L RBF equipped with oil bath; overhead stirrer; normal Condenser; nitrogen blanket and water scrubber. Reaction mass is heated slowly to 90° C. to attain molten slurry mass before stirring the mass with agitator and heating was continued slowly. N,N-dimethyl formamide was charged once reaction mass attain 100° C. either at once or in lot-wise throughout temperature ramp to reaction conversion temperature (160° C.). After attaining the reaction mass temperature, it is maintained for 5-6h at 160° C. and further heated to 170° C. for another 5-6h to attain conversion of 2,3-Dichloronitrobenzene to <5%. Reaction mass is cooled to 90° C.; N,N-Dimethyl formamide is recovered by vacuum distillation. Crude 2-Chloro-6-Nitrobenzonitrile is diluted with monochlorobenzene at 80° C.; at this temperature, inorganic salts are removed by vacuum filtration. Additional hot monochlorobenzene is added to wash and completely remove the organic mass from inorganic residue. Organic Filtrate containing product is washed with 5% Aqueous Ammonia solution at 70° C. for 1 hour, layer separated & neutralized by another 10% Aq. HCl and water wash at 70° C.; charcoal treated at 70° C. Wash treated Organic filtrate is subjected to monochlorobenzene recovery and reaction mass cooled to 10° C. and filter the precipitated product on vacuum filtration wash it with cold solvent. Unload the wet cake & dry it at 80° C.

TABLE 5

| Impact of DMF Catalyst ratio on conversion of 2,3-DCNB to CNBN & impurity formation | | | | | |
|---|---|---|---|---|---|
| Expt. No. | (#) | 1 | 2 | 3 | 4 |
| 2,3-DCNB | (mol) | 2.59 | 2.59 | 2.59 | 10.4 |
| CuCN | (mol) | 0.777 | 0.777 | 0.777 | 4.05 |
| NaCN | (mol) | 2.072 | 2.072 | 2.072 | 5.3 |
| DMF Catalyst | (g/mol of 2,3-DCNB) | 193 | 96.5 | 27 | 28.8 |
| Temp | (° C.) | 170 | 170 | 170 | 160 |
| Reaction Time | (h) | 6 | 8 | 8 | 10 |
| Reaction mass | MNCB (%) | 18.38 | 12.8 | 5.1 | 1.5 |
| composition | 2,3-DCNB (%) | 32.43 | 18.9 | 1.9 | 1.6 |
|  | CNBN (%) | 41.71 | 66.7 | 91.8 | 96.6 |

These examples demonstrate that lowering the charge of DMF from 193 g/mol of 2,3-DCNB to 27-28 g/mol of 2,3-DCNB dramatically improves the reaction performance, i.e. the CNBN content improves from 41% to 91-96%.

TABLE 6

Use of Sodium Cyanide/Copper Chloride reagent for CNBN conversion

| Expt no, | (#) | 1 | 2 |
|---|---|---|---|
| 2,3-DCNB | (mol) | 2.59 | 2.59 |
| NaCN | (mol) | 2.85 | 2.85 |
| CuCl | (mol) | 1.33 | 1.33 |
| Catalyst | (DMF, g) | 75 | 75 |
| Temp | (° C.) | 170 | 160 |
| Reaction Time | (h) | 16 | 18 |
| Reaction mass composition | MNCB (%) | 1.35 | 3.2 |
| | 2,3-DCNB (%) | 2.4 | 7.2 |
| | CNBN (%) | 95.4 | 87.03 |
| Product Quality | MNCB (%) | Not detected | Not detected |
| | 2,3-DCNB (%) | Not detected | Not detected |
| | CNBN (%) | 99.7 | 99.9 |
| Yield | (%) | 79.2 | 82.4 |

Copper cyanide is expensive and very poorly soluble in most organic solvents which makes it a poor choice for reactivity. By replacing it with copper chloride the system is more amenable for commercial manufacture at reduced cost.

As described herein, these problems and others in this area are addressed by the invention described herein. Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A process for producing 2,6-dichlorobenzonitrile comprising
    a) cyanating 1,2-dichloro-3-nitro benzene in the presence of a catalytic amount of an aprotic amide to obtain 2-chloro-6-nitrobenzonitrile, wherein step a) is carried out in presence of sodium cyanide and copper cyanide, or sodium cyanide and copper chloride, or a mixture of sodium cyanide, copper chloride and copper cyanide, and
    b) de-nitrochlorinating 2-chloro-6-nitrobenzonitrile with chlorine gas to obtain 2,6-dichlorobenzonitrile, wherein step (b) is performed for 5 to 15 hours without solvent and a molar ratio of 2-chloro-6-nitrobenzonitrile to chlorine gas is from 1:1 to 1:5.

2. The process as claimed in claim 1 is carried out at temperature in a range of 100° C.–200° C.

3. The process as claimed in claim 1 wherein said 2,6-dichlorobenzonitrile is substantially free from $NO_x$ or 2-chlorobenzonitrile or 1,2,3-trichlorobenzonitrile or tetrachlorobenzene or 2,6-dichlorobenzamide.

4. The process of claim 1, wherein the 2,6-dichlorobenzonitrile is produced at a yield of at least 80% and a purity of at least 99%.

5. The process of claim 1, wherein step b) takes place for 8 to 11 hours at 150° C. to 200° C.

6. The process of claim 1, wherein step b) takes place for 9 to 10 hours at 190° C. to 200° C.

7. The process of claim 1 wherein the aprotic amide is selected from N,N-dimethylformamide, dimethylsulfoxide, N,N-dimethylacetamide, hexamethylphosphoramide, or N-methylpyrrolidone.

* * * * *